(12) United States Patent
Marshall

(10) Patent No.: US 10,413,721 B2
(45) Date of Patent: Sep. 17, 2019

(54) SYSTEM AND METHOD FOR IMPLANTABLE MEDICAL DEVICE LEAD SHIELDING

(71) Applicant: MEDTRONIC, INC., Minneapolis, MN (US)

(72) Inventor: Mark T. Marshall, Forest Lake, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 37 days.

(21) Appl. No.: 15/676,279

(22) Filed: Aug. 14, 2017

(65) Prior Publication Data

US 2017/0368335 A1   Dec. 28, 2017

Related U.S. Application Data

(62) Division of application No. 14/715,271, filed on May 18, 2015, now Pat. No. 9,731,119, which is a division of application No. 12/112,889, filed on Apr. 30, 2008, now Pat. No. 9,037,263.

(60) Provisional application No. 61/035,956, filed on Mar. 12, 2008.

(51) Int. Cl.
| | |
|---|---|
| *A61N 1/00* | (2006.01) |
| *A61N 1/05* | (2006.01) |
| *A61N 1/04* | (2006.01) |
| *A61N 1/08* | (2006.01) |

(52) U.S. Cl.
CPC ............ *A61N 1/0563* (2013.01); *A61N 1/048* (2013.01); *A61N 1/0472* (2013.01); *A61N 1/08* (2013.01); *A61N 1/086* (2017.08)

(58) Field of Classification Search
None
See application file for complete search history.

(56) References Cited

U.S. PATENT DOCUMENTS

| | | | | |
|---|---|---|---|---|
| 7,822,484 B1 * | 10/2010 | Zhao | ............. | A61N 1/056 600/375 |
| 7,853,332 B2 * | 12/2010 | Olsen | ............. | A61N 1/0529 607/116 |
| 7,941,226 B2 * | 5/2011 | Marshall | ............. | A61N 1/05 607/116 |
| 8,825,180 B2 * | 9/2014 | Bauer | ............. | A61N 1/056 607/116 |

(Continued)

*Primary Examiner* — Amanda K Hulbert
*Assistant Examiner* — Elizabeth K So
(74) *Attorney, Agent, or Firm* — Withers & Keys, LLC

(57) ABSTRACT

An implantable medical device (IMD) can include a cardiac pacemaker or an implantable cardioverter-defibrillator (ICD). Various portions of the IMD, such as a device body, a lead body, or a lead tip, can be provided to reduce or dissipate a current and heat induced by various external environmental factors. According to various embodiments, features can be incorporated into the lead body, the lead tip, or the IMD body to reduce the creation of an induced current, or dissipate the induced current and heat created due to an induced current in the lead. For example, an IMD can include at least one outer conductive member and a first electrode. The first electrode can be in electrical communication with the at least one outer conductive member. The first electrode can dissipate a current induced in the at least one outer conductive member via a first portion of the anatomical structure.

6 Claims, 6 Drawing Sheets

(56) References Cited

U.S. PATENT DOCUMENTS

| | | | |
|---|---|---|---|
| 9,901,731 B2* | 2/2018 | Marshall ................ | A61N 1/056 |
| 2009/0171421 A1* | 7/2009 | Atalar .................... | A61N 1/056 607/63 |

* cited by examiner

SYSTEM AND METHOD FOR IMPLANTABLE MEDICAL DEVICE LEAD SHIELDING

CROSS-REFERENCE

This application claims the benefit of U.S. Provisional Application No. 61/035956, filed on Mar. 12, 2008. The disclosure of the above application is incorporated herein by reference.

FIELD

The present disclosure relates to implantable medical devices (IMDs), in particular to a system and method for shielding a cardiac lead system from radio frequency (RF) energy.

BACKGROUND

The statements in this section merely provide background information related to the present disclosure and may not constitute prior art.

The human anatomy includes many types of tissue that can either voluntarily or involuntarily, perform certain functions. However, after disease or injury, certain tissues may no longer operate within general anatomical norms. For example, after disease, injury, age, or combinations thereof, the heart muscle may begin to experience certain failures or deficiencies. Some of these failures or deficiencies can be corrected or treated with IMDs. These devices can include implantable pulse generator (IPG) devices, pacemakers, implantable cardioverter-defibrillator (ICD) devices, cardiac resynchronization therapy defibrillator devices, or combinations thereof.

One of the main portions of the IMD can include a lead that is directly connected to tissue to be affected by the IMD. The lead can include a tip portion that is directly connected to the anatomical tissue, such as a muscle bundle, and a lead body that connects to the device body or therapeutic driving device. It is generally known that the device body or case portion can be implanted in a selected portion of the anatomical Structure, such as in a chest or abdominal wall, and the lead can be inserted through various venous portions so that the tip portion can be positioned at the selected position near or in the muscle group.

The IMD generally remains with the patient during the rest of the patient's natural life. To that end, the IMD can be exposed to various environmental factors. For example, the patient may undergo a magnetic resonance imaging (MRI) procedure or other high frequency imaging procedures. In this case, portions of the IMD may act as an antenna and have current and thermal energy induced therein due to the MRI procedure. Accordingly, reduction or dissipation of the induced current or thermal energy may be useful in certain circumstances.

SUMMARY

An implantable medical device (IMD) can include implantable pulse generator (IPG) devices, implantable cardioverter-defibrillators (ICD), cardiac resynchronization therapy defibrillator devices, neurostimulators or combinations thereof. The IMD can be positioned in a selected portion of the anatomical structure, such as a chest wall or abdominal wall, and a lead can be positioned through a vein or transvenously so that a lead tip can be implanted in a portion of the cardiac or heart muscle. Various portions of the IMD, such as a case or device body, the lead body, or the lead tip, can be formed or augmented to reduce or dissipate heat production due to various external environmental factors. For example, a magnetic and/or electric field from a magnetic resonance imager (MRI), diathermy (including shortwave, microwave, ultrasound, or the like) or other energy field producing devices can induce currents in the lead. According to various embodiments, features or portions can be incorporated into the lead body, the lead tip, or the device body to reduce the creation of an induced current, or dissipate or increase the area of dissipation of thermal energy created due to an induced current in the lead.

An implantable medical device operable to provide a therapy to an anatomical structure is provided. The device can include a lead having a proximal end, a distal end and at least one outer conductive member and a multilumen member that extends from the proximal end to the distal end. The device can also include a first electrode fixedly coupled between the proximal end and the distal end of the lead such that the first electrode can be positioned adjacent to a first portion of the anatomical structure, the first electrode in electrical communication with a first inner conductor disposed within the multilumen member to deliver a therapy to the first portion of the anatomical structure. The first electrode can be in electrical communication with the at least one outer conductive member and can have a first surface area. The device can also include a second electrode that can be coupled to the distal end of the lead. The second electrode in electrical communication with a second inner conductor disposed within the multilumen member to deliver a therapy to a second portion of the anatomical structure. The second electrode can have a second surface area. The first surface area can be greater than the second surface area. The first electrode can dissipate a current induced in the at least one outer conductive member via the first portion of the anatomical structure.

Provided is an implantable medical device operable to provide a therapy to an anatomical structure. The device can include a therapy device implanted in a portion of the anatomical structure and operable to generate the therapy for the anatomical structure. The device can also include a lead having a proximal end, a distal end and a lead body that includes a first outer conductive braid, a second outer conductive braid and a multilumen member. The first outer conductive braid and the second outer conductive braid can be disposed about the multilumen member. The device can include a first electrode fixedly coupled between the proximal end and the distal end of the lead such that the first electrode is positioned adjacent to a first portion of the anatomical structure. The first electrode can be in communication with the first outer conductive braid and the second outer conductive braid. The device can also include a first inner conductor that can pass through a portion of the multilumen member. The first inner conductor can be in electrical communication with the first electrode to deliver a therapy to the first portion of the anatomical structure. The device can include a tip electrode extending beyond the distal end of the lead arid a tip inner conductor that can pass through a portion of the multilumen member. The tip inner conductor can be in electrical communication with the tip electrode to deliver a therapy to a second portion of the anatomical structure. The device can include a second electrode coupled adjacent to the tip electrode at the distal end of the lead such that the second electrode is positioned adjacent to a third portion of the anatomical structure. The device can further include a second inner conductor that can pass through a portion of the multilumen member. The second inner conductor can be in electrical communication with the second electrode to deliver a therapy to the third portion of the anatomical structure. The first outer conductive braid can be disposed between the proximal end of the lead and the first electrode, and the second outer conductive braid can be disposed between the first electrode and the second electrode. The first electrode can dissipate a current induced in the first outer conductive braid and second outer conductive braid, via the first portion of the anatomical structure.

Further provided is a method of forming a cardiac lead system for implantation into an anatomical structure. The method can include providing a lead having a multilumen member that can pass; through the lead, a first electrode in electrical communication with a first inner conductor and fixedly coupled to the multilumen member, the first inner conductor passing through a portion of the multilumen member, and a second electrode in electrical communication with a second inner conductor and extending beyond an end of the multilumen member, the second inner conductor passing through a portion of the multilumen member. The method can also include providing the first electrode with a first surface area and the second electrode with a second surface area, with the first surface area being larger than the second surface area. The method can include covering a substantial portion of the lead with a shield, and electrically coupling the shield to the first electrode.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
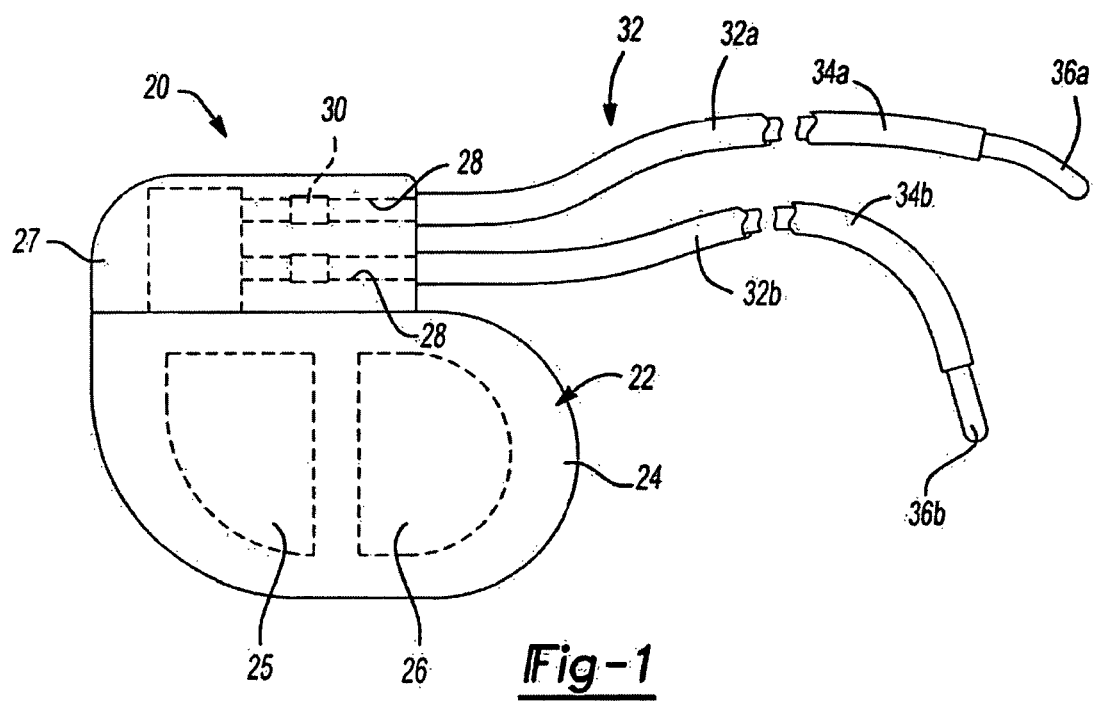
FIG. 1 is a view of an IMD including a lead connected to a device body.

The following description is merely exemplary in nature and is not intended to limit the present disclosure, application, or uses. It should be understood that throughout the drawings, corresponding reference numerals indicate like or corresponding parts and features. As indicated above, the present teachings are directed towards providing a system and method for shielding a cardiac lead system from RF energy. It should be noted, however, that the present teachings could be applicable to any appropriate procedure in which it is desirable to shield a component from external electrical fields. Therefore, it will be understood that the following discussions are not intended to limit the scope of the appended claims.

With reference to FIG. 1, an implantable medical device (IMD) 20, which can include implantable pulse generator (IPG) devices, implantable cardioverter-defibrillator (ICD) devices, cardiac resynchronization therapy defibrillator devices, or combinations thereof, is exemplarily illustrated. The IMD 20 can include an implantable case or body assembly 22 The implantable case 22 can be formed of appropriate materials and include appropriate features, such as a hermetically sealed body wall 24. The body wall 24 can be made of a substantially inert material or of a conducting material.

Figure 2:
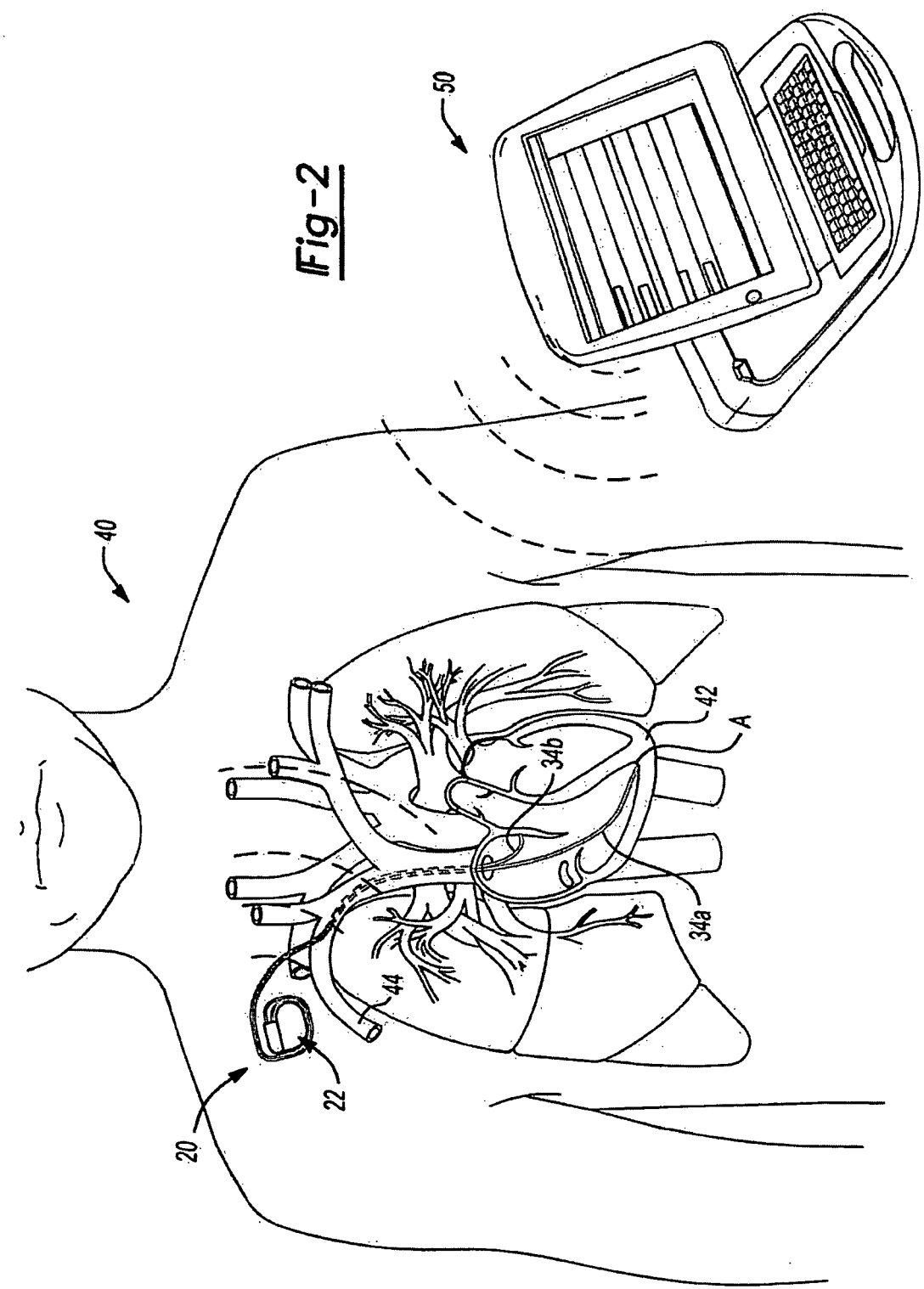
FIG. 2 is a simplified environmental view of an IMD implanted in a patient.

Contained within or associated with the case 22 can be a power device 25 (i.e., battery), a controller assembly 26, and a connector body 27. The controller assembly 26 can include a circuit board having a processor, memory, transmitter, receiver, and other appropriation portions, further discussed herein. The connector body 27 can extend from or be integrated with the case 22. The connector body 27 can include multiple ports 28 that each interconnect with a connector terminal 30 of a lead assembly 32. FIG. 1 illustrates two lead assemblies 32a, 32b where each lead assembly 32a, 32b includes lead bodies 34a, 34b extending from tip electrodes 36a, 36b. Although the IMD 20 is illustrated in FIGS. 1 and 2 as including two lead assemblies 32a, 32b, it will be understood that any number of lead assemblies 32 could be employed with the IMD 20 depending upon the malady of the patient and the particular IMD 20 employed. Moreover, the switch assembly further discussed herein can be associated with one or all of the lead assemblies 32a, 32b for the particular IMD 20 employed.

A fixation mechanism can also be included with each lead assembly 32a, 32b to affix each tip electrode 36a, 36b relative to or in a selected tissue of the patient. The fixation mechanism can be near each tip electrode 36a, 36b or define a portion of the tip electrode 36a, 36b. Fixation mechanisms can be any appropriate type, including a grapple mechanism, a helical mechanism, a drug-coated connection mechanism, and other appropriate connection mechanisms.

A majority of each lead body 34a, 34b can also be formed in a generally known and selected manner. For example, the various conductors and electrical components can be encased in silicone, polyurethane, and other appropriate materials. For example, at least one inner conductor 136 (FIG. 5) can extend from each connector terminal 30 to engage each tip electrode 36a, 36b (identified as 132d in FIG. 4). It will be understood by one skilled in the art, the inner conductor 136 can be one piece or multiple components that are interconnected. Also, more than one conductor can be provided, such as one conductor for each electrode in each lead assembly 32a, 32b. The inner conductor 136 can also be cannulated or include a solid or non-cannulated cable. The casing material of each lead body 34a, 34b can electrically insulate the inner electrical conductor from an external environment.

The IMD 20, including the components discussed above; can be implanted in a patient 40 as illustrated in FIG. 2. The IMD 20 can include one or more lead assemblies 32, such as the first lead assembly 32a and the second lead assembly 32b. The first lead assembly 32a arid the second lead assembly 32b can be connected to the connector body 27. As one skilled in the art will understand, the position of lead bodies 34a, 34b can depend upon the type of IMD and the malady of the patient 40. For example, the lead assemblies 32a, 32b can be positioned transvenously to positions within a heart 42 or on the outside of the heart 42. The IMD 20 can be provided to pace the heart 42, defibrillate the heart 42, sense conditions of the heart 42, etc.

The IMD 20, including the case 22 and the lead bodies 34a, 34b, can be implanted using known procedures. For example, an incision can be made in a chest wall or an abdomen wall of the patient 40 and the lead assemblies 32a, 32b can be passed through selected veins to selected portions of the heart 42 of the patient 40. The case 22 can also be positioned through the incision into a chest wall or abdominal wall of the patient 40. In a selected procedure, the leads assemblies 32a, 32b can be passed through a superior vena cava 44 of the patient 40. The lead tips or tip electrodes 36a, 36b can be positioned at various positions in the heart 42, such as at the ventricles or atriums thereof. The position of the lead assemblies 32a, 32b and tip electrodes 36a, 36b can be selected for pacing, defibrillation, sensing, or other appropriate procedures. The specific implantation procedure, position of the tip electrodes 36a, 36b, and the like can depend upon the patient 40, the surgeon performing the procedure, the specifics of the lead assemblies 32a, 32b, or other considerations.

As discussed above, the IMD 20, including the case 22 and the lead assemblies 32a, 32b can include various features or controls to defibrillate or pace the heart 42. The controls can include a processor associated with the controller assembly 26 located within the case 22. The processor can be programmed to control driving a current through the lead bodies 34a, 34b to the tip electrodes 36a, 36b to defibrillate or pace the heart 42.

With continued reference to FIG. 2, a programmer or programming system 50 can be provided. The programmer 50 can include a telemetry system that is operable to wirelessly transmit a signal to the processor within the case 22. It will be understood that a wired communication system can also be used. In addition, an induction system can be used where a coil is positioned near the case 22 and a signal is sent from the programmer 50 via induction. The programmer 50 can also receive information from the IMD 20 (e.g. tachycardia rhythms, times and programming settings) to assist in providing an appropriate program for therapy and to determine if the IMD 20 is operating properly. The programmer 50 can include any appropriate programming system, including one generally known to those skilled in the art, such as the Medtronic CARELINK™ programmer, sold by Medtronic, Inc. of Minneapolis, Minn.

Moreover, the IMD 20, including the case 22 and the lead assemblies 32a, 32b, can be formed to counteract or interact with various environmental factors. For example, the lead assemblies 32a, 32b can include features or portions to re-direct or dissipate thermal energy created by an induced current. Induced currents can be created due to an external field, such as an electromagnetic field acting on the conductors of the lead assemblies 32a, 32b.

For example, according to various embodiments, the patient 40 which has the implanted IMD 20 may receive a certain therapy or diagnostic technique, such as a magnetic resonance image (MRI) scan. Although not illustrated, a MRI, generally understood by one skilled in the art, uses high frequency electromagnetic pulses and strong magnetic fields to create image data regarding the patient 40. Generally, a MRI will have a frequency of about 42 MHz per tesla. Many common MRI systems use about 1.5 tesla magnetic fields and have a corresponding RF frequency of about 63 MHz. Without being bound by the theory, the strong magnetic fields in a MRI can induce aligned spins of sub-atomic particles arid the high frequency RF pulses can be used to change the alignment or otherwise affect the sub-atomic particles within the patient 40.

The strong magnetic fields and electromagnetic pulses may induce currents within the lead assemblies 32a, 32b of the IMD 20. The current induced in the lead assemblies 32a, 32b may cause certain affects, including heating, of the various lead components. According to various embodiments, such as those discussed herein, components, controls and/or mechanisms can be provided to reduce or eliminate the amount of current or thermal energy induced within each tip electrode 36a, 36b, or increase an area over which the current or thermal energy can be; dissipated.

Figure 3:
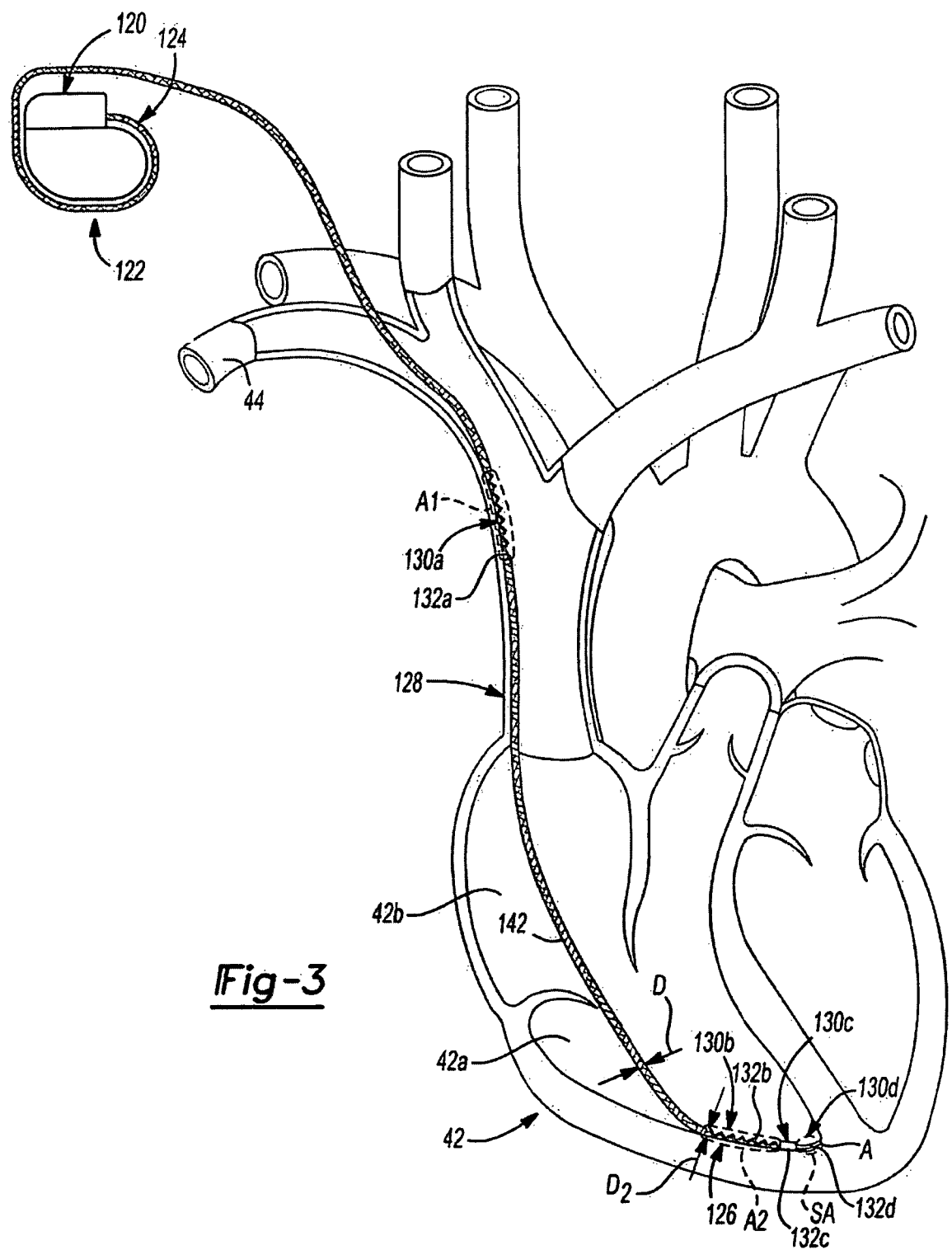
FIG. 3 is an environmental view of an ICD implanted in a patient that includes an exemplary shielded cardiac lead system.

According to various embodiments, with reference to FIG. 3, the IMD 20 can comprise an implantable cardiac device, such as an implantable cardioverter-defibrillator (ICD) 120. As the ICD 120 that will be described herein with reference to FIGS. 3-6 can be similar to the IMD 20 described with reference to FIGS. 1-2, similar reference numerals will be used to denote like components. With continued reference to FIG. 3, the ICD 120 can be used to detect and treat cardiac arrhythmias, and thus, can deliver a therapy to a desired location within the heart 42. In this regard, the ICD 120 can provide anti-tachycardia pacing, cardioversion, defibrillation, and/or bradycardia pacing, while also monitoring the heart rhythm to determine if a therapy is needed. As the ICD 120 can comprise any suitable ICD, such as the ENTRUST™ family of ICDs available from Medtronic, Inc. of Minneapolis, Minn., the ICD 120 will not be discussed in great detail herein. Briefly, however, the ICD 120 can include at least one ICD lead 122, which can be implanted into an anatomical structure, such as the heart 42. The ICD 120 can comprise a single chamber ICD that includes one lead 122 (as illustrated), a dual chamber ICD that includes two leads or a biventricular ICD that includes three leads. The lead 122 can both sense the electrical activity of the heart 42 and can also deliver electrical energy to pace the heart 42. The lead 122 can include a proximal end 124, a distal end 126, a body 128 and at least one electrode assembly 130.

As will be discussed further herein, each electrode assembly 130 can include an electrode 132 and a transmission member 134, which includes an inner conductor 136 and an insulative member 138. Briefly, the electrode 132 can be in contact with the anatomical structure to deliver a therapy to the anatomical structure, such as an electrical pulse, and can be in communication with the inner conductor 136 to receive the therapy. Thus, the inner conductor 136 can be in electrical communication with the electrode 132 and the ICD 120 to receive the therapy. In this example, the lead 122 can include four electrode assemblies 130, labeled 130a, 130b, 130c, 130d from the proximal end 124 to the distal end 126 of the lead 122. It should be noted that while the lead 122 is illustrated with four electrode assemblies 130 in FIG. 3, the lead 122 may have any number of electrode assemblies 130.

The proximal end 124 of the lead 122 can include a connector portion 140. As the connector portion 140 can be generally known, the connector portion will not be discussed in great detail herein. Briefly, however, the connector portion 140 can electrically couple the lead 122 to the ICD 120. the distal end 126 can terminate within the anatomical structure adjacent to the desired location for the delivery of the therapy, and generally, for example, can terminate adjacent to an apex of the heart 42, such as the right ventricular apex A, a ventricle, such as the right ventricle 42a, or other chambers, such as the right atria 42b, of the heart 42. As will be discussed, one electrode 132 of the at least one electrode assembly 130 can be coupled to the distal end 126 to deliver a therapy to the atrium A of the heart 42.

The body 128 of the lead 122 can extend from the proximal end 124 to the distal end 126. With reference FIG. 5, the body 128 can include an overlay 142, at least one conductive member or shield 144, and a multilumen member 146. The body 128 can serve to protect, carry and guide the at least one electrode assembly 130 through the anatomical structure. The overlay 142 can comprise any suitable biocompatible material, such as a biocompatible polymer, and can generally be composed of polyurethane. The overlay 142 can be disposed over and coupled to the at least one conductive member 144. For example, the overlay 142 can be formed onto the at least one conductive member 144 such that the overlay 142 is molded onto and penetrates through the at least one conductive member 144 thereby encapsulating the at least one conductive member 144 within the overlay 142 (illustrated in phantom in FIG. 5).

The at least one conductive member 144 can comprise a first conductive braid 144a and a second conductive braid 144b. The at least one conductive member 144 can generally extend for a majority of a length of the lead 122, and can generally be electrically coupled to the electrode 132 positioned near a proximal end 124 of the lead 122. It will be understood that although the at least One conductive member 144 is illustrated arid described herein as comprising a braid, the at least one conductive member 144 could also comprise any desired shape or structure, such as a coil, continuous tubular structure, etc., and thus, need not be composed of a plurality of interwoven conductive members as shown. The first conductive braid 144a can extend from the proximal end 124 of the lead 122 to the electrode assembly 130 located near a proximal end of the electrode assembly 130a. The second conductive braid 144b can extend from a distal end of the electrode assembly 130a to a proximal end of a second electrode assembly 130b. The first conductive braid 144a and the second conductive braid 144b can each be in electrical communication with the electrode 132a of the first electrode assembly 130a to dissipate a current induced in the first conductive braid 144a and the second conductive braid 144b through the electrode 132a.

Figure 6:
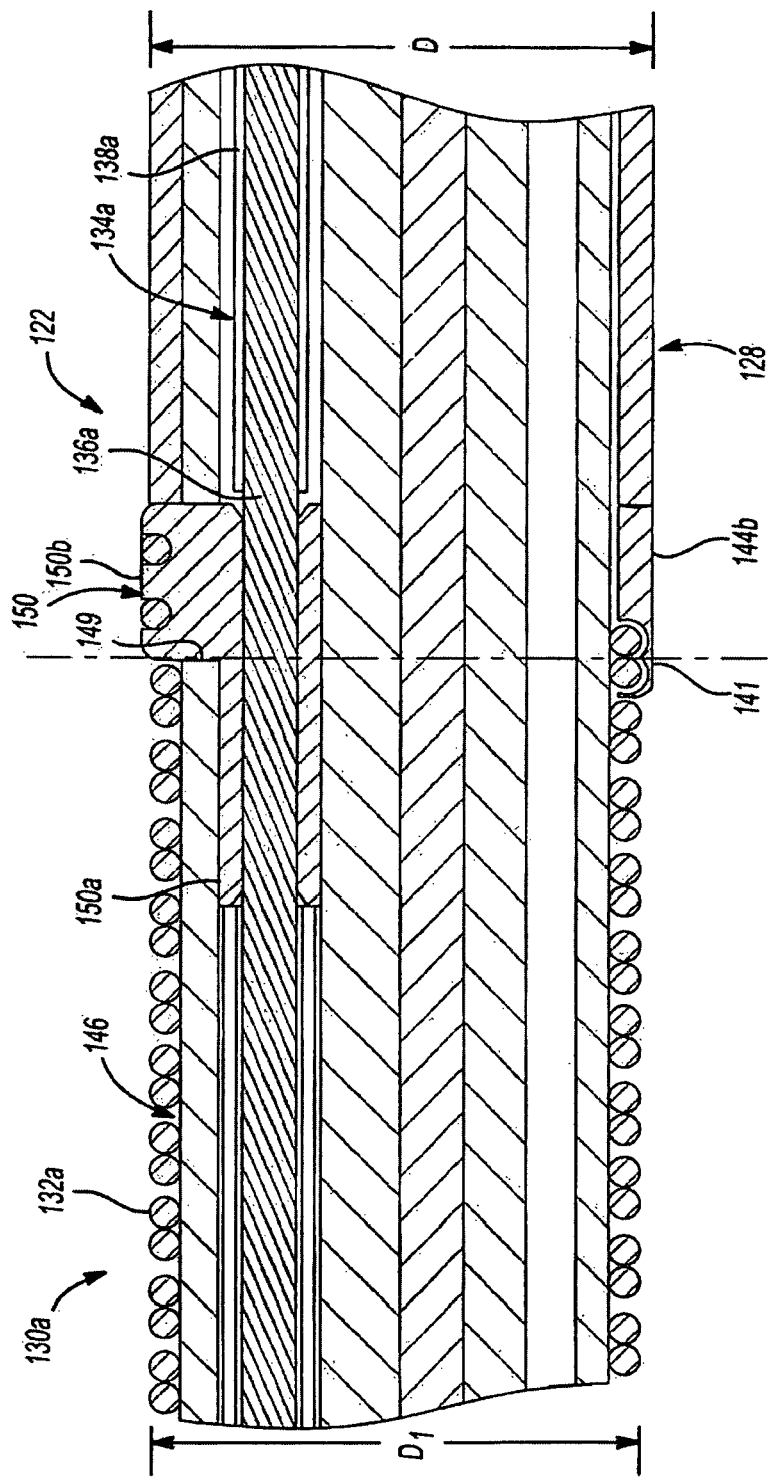
FIG. 6 is a cross-sectional view of the cardiac lead system of FIG. 4 taken along line 6-6 of FIG. 4.

The multilumen member 146 can be disposed within the first conductive braid 144a and the second conductive braid 144b. The multilumen member 146 can define at least one channel 148 for receipt of each of the inner conductors 136 associated with the electrode assemblies 130. Generally, the multilumen member 146 can be composed of a biocompatible material, such as a biocompatible polymer, for example, a silicone rubber. The at least one channel 148 can receive each of the inner conductors 136 of the electrode assemblies 130, arid can serve as a conduit that guides each of the inner conductors 136 from the ICD 120 to the electrode 132 of the respective electrode assembly 130. With reference to FIG. 6, the multilumen member 146 can also include one or more apertures 149 that extend out of a sidewall of the multilumen member 146. The apertures 149 can enable the various electrode assemblies 130 to be electrically coupled to the inner conductors 136 passing through the multilumen member 146.

With reference to FIGS. 3-6, selected ones of the electrode assemblies 130 can be operable to deliver the therapy to the anatomical structure, and a selected one of the electrode assemblies 130 can be operable to sense electrical activity at a desired site in the anatomical structure. The electrode assemblies 130 can include a first electrode or first defibrillator electrode assembly 130a, a second electrode or second defibrillator electrode assembly 130b, a sense electrode or ring electrode assembly 130c and a tip electrode assembly 130d.

Figure 4:
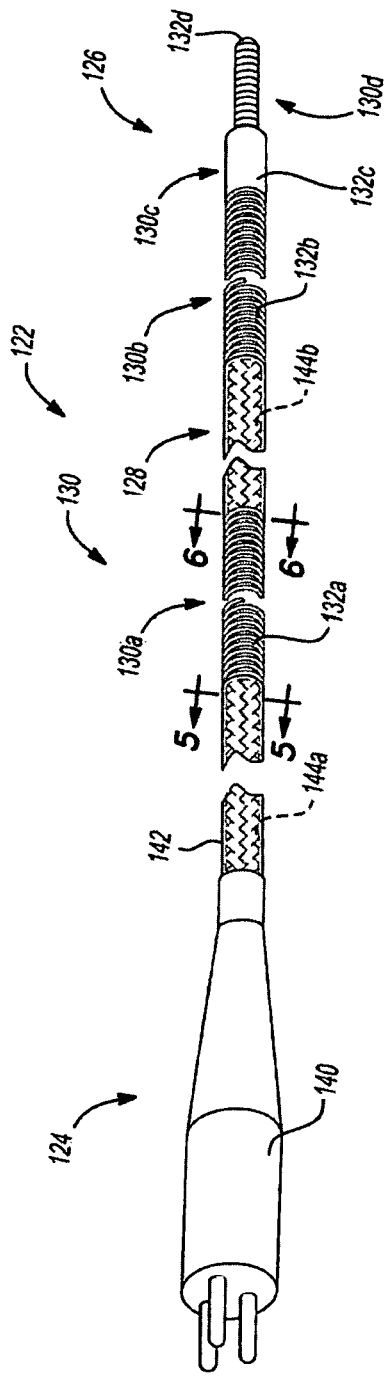
FIG. 4 is a perspective view of the exemplary shielded cardiac lead system according to various embodiments.
Figure 5:
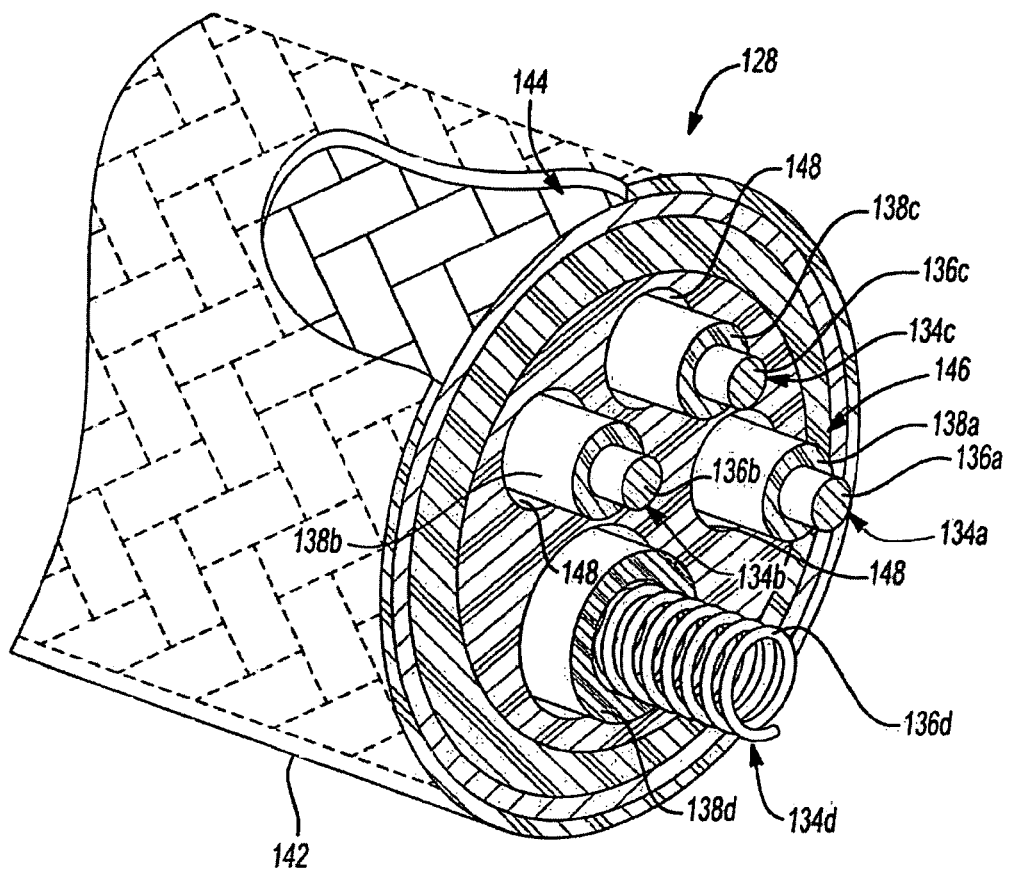
FIG. 5 is a perspective cut away view of the cardiac lead system of FIG. 4 taken along line 5-5 of FIG. 4.

With reference to FIGS. 4-6, the first defibrillator electrode assembly 130a can be coupled to the body 128 such that the first defibrillator electrode assembly 130a can be disposed between the proximal end 124 and the distal end 126. The first defibrillator electrode assembly 130a can include the first defibrillator electrode 132a and transmission member 134a. Generally, the first defibrillator electrode assembly 130a can be coupled to the body 128 such that when the lead 122 is implanted within the anatomical structure, such as the heart 42, the first defibrillator electrode 132a can be adjacent to a first portion of the anatomical structure, such as the superior vena cava 44 (FIG. 3).

With reference to FIGS. 3 and 6, the first defibrillator electrode 132a can have a first diameter D1 and a first surface area (generally indicated as A1 in phantom). The first diameter D1 can be substantially equivalent to a diameter D of the overlay 142 so that when the first defibrillator electrode 132a is coupled to the body 128, a smooth transition exists between the first defibrillator electrode 132a and the body 128. The first surface area A1 can be larger than a surface area of the electrode 132d of the distalmost electrode assembly 130d; generally indicated as SA in phantom. Generally, the first surface area A1 can range from about 400 square millimeters to about 1000 square millimeters, and generally can range from about 750 square millimeters to about 850 square millimeters. As shown in FIG. 6, the first defibrillator electrode 132a can be coupled to the at least one conductive member 144, the multilumen member 146 of the body 128, and the transmission member 134a. The transmission member 134a can pass through one of the channels 148 of the multilumen member 146, and can be in communication with and responsive to the ICD 120 to transmit an electrical signal or charge to the first defibrillator electrode 132a. The transmission member 134a can include the inner conductor 136a that is encased by or coated with an insulative member 138a, such as a biocompatible polymer, for example, a fluoropolymer.

With reference to FIGS. 4 and 6, the first defibrillator electrode 132a can be coupled to and in communication with the first conductive braid 144a and the second conductive braid 144b (FIG. 6). Generally, the location of the first defibrillator electrode assembly 130a can be fixed relative to a length of the lead 122 between the proximal end 124 and the distal end 126. The first defibrillator electrode 132a can be coupled to the first conductive braid 144a and the second conductive braid 144b, via any suitable mechanism that enables electrical communication between the first defibrillator electrode 132a, the first conductive braid 144a and the second conductive braid 144b. These mechanisms can include welding, crimping, conductive adhesives, conductive fasteners, etc., as generally indicated by reference numeral 141 in FIG. 6.

Accordingly, if a current is induced in the first conductive braid 144a and/or second conductive braid 144b from an external electric field, such as that generated by an MRI, the current and heat generated by the induced current can flow from the first conductive braid 144a and/or second conductive braid 144b into the first defibrillator electrode 132a, which is grounded by the body. With reference to FIG. 3, as the first defibrillator electrode 132a is adjacent to the anatomical structure, such as the superior vena cava 44, and has a large surface area A1, the current can be dissipated by the first defibrillator electrode 132a into the anatomical structure. This can ensure that if a current is induced in the first conductive braid 144*a* and/or second conductive braid 144*b*, any induced current flows to the electrode assembly 130 that has the largest surface area, such as the first defibrillator electrode assembly 130*a*. In other words, the at least one outer conductive member or shield 144 shields and prevents currents from being induced in the inner conductors 136 which are surrounded by the at least one outer conductive member or shield 144, thereby preventing induced currents from flowing to a smaller surface electrode assembly 130, such as the tip electrode 132*d*.

With reference to FIG. 6, the first defibrillator electrode 132*a* can be coupled to the transmission member 134*a* disposed in the multilumen member 146 via a connection 150. The connection 150 can couple the first defibrillator electrode 132*a* to the inner conductor 136*a* to enable electrical communication between the inner conductor 136*a* and the first defibrillator electrode 132*a*, The connection 150 can include a first end 150*a* and a second end 150*b*. The first end 150*a* can be crimped to the inner conductor 136*a* of the transmission member 134*a*, while the second end 150*b* can be coupled to the first defibrillator electrode 132*a*, through welding, for example.

With reference to FIGS. 3 and 4, the second defibrillator electrode assembly 130*b* can be coupled to the body 128 such that the second defibrillator electrode assembly 130*b* can be disposed near the distal end 126 of the lead 122, between the first electrode assembly 130*a* and the ring electrode assembly 130*c*. Generally, the location of the second defibrillator electrode assembly 130*b* can be fixed relative to the length of the lead 122 between the proximal end 124 and the distal end 126. The second defibrillator electrode assembly 130*b* can include the second defibrillator electrode 132*b* and the transmission member 134*b*. Generally, the second defibrillator electrode assembly 130*a* can be coupled to the body 128 such that when the lead 122 is implanted within the anatomical structure, such as the heart 42, the second defibrillator electrode 132*b* cart be adjacent to a second portion of the anatomical structure, such as a right ventricle 42*a* of the heart 42 (FIG. 3).

With reference to FIG. 3, the second defibrillator electrode 132*b* can have a second diameter D2 and a second surface area (generally indicated as A2 in phantom). The second diameter D2 can be substantially equivalent to the diameter D of the overlay 142 so that when the second defibrillator electrode 132*b* is coupled to the body 128, a smooth transition exists between the second defibrillator electrode 132*b* and the body 128. The second surface area A2 can be larger than the surface area SA of the tip electrode assembly 130*d*, but can be smaller than the first surface area A1 of the first defibrillator electrode 132*a*. Generally, the second surface area A2 can range from about 300 square millimeters to about 800 square millimeters, and generally can range from about 500 square millimeters to about 650 square millimeters.

The second defibrillator electrode 132*b* can be adjacent to, but not in electrical communication with the at least one conductive member 144, and can be coupled to the multilumen member 146 of the body 128, and the transmission member 134*b*. As the second defibrillator electrode 132*b* can be adjacent to, but not in electrical communication with the second conductive braid 144*b*, this can ensure that if a current is induced in the second conductive braid 144*b*, the current is communicated to the first defibrillator electrode 132*a*, which has a larger surface area A1 to dissipate the current, and can dissipate the current in a generally non-critical area of the anatomical structure. The transmission member 134*b* can pass through one of the channels 148 of the multilumen member 146, and the inner conductor 136*b* can be in communication with and responsive to the ICD 120 to transmit an electrical signal or charge to the second defibrillator electrode 132*b*. The inner conductor 136*b* can be encased by or coated with the insulative member 138*b*, which can comprise a biocompatible polymer, for example a fluoropolymer, The second defibrillator electrode 132*b* can be coupled to the inner conductor 136*b* disposed in the multilumen member 146 via a suitable connection, such as the connection 150 (not specifically shown). In this regard, if employed, the connection 150 can electrically couple the second defibrillator electrode 132*b* to the inner conductor 136*b*. As the connection 150 between the inner conductor 136*b* and the second defibrillator electrode 132*b* can be substantially similar to that discussed with regard to the first defibrillator electrode assembly 130*a*, the connection 150 will not be discussed with regard to the second defibrillator electrode assembly 130*b*.

reference to FIGS. 3 and 4, the sense electrode or ring electrode assembly 130*c* can be coupled to the body 128 such that the ring electrode assembly 130*c* can be disposed near the distal end 126, between the second electrode assembly 130*b* and the tip electrode assembly 130*d*. As the ring electrode assembly 130*c* can be generally known in the art, and can be similar to the ring electrode assembly of the SPRINT QUATTRO SECURE™ cardiac lead commercially available from Medtronic, Inc. of Minneapolis, Minn., the ring electrode assembly 130*c* will not be discussed in great detail herein. Briefly, however, the ring electrode assembly 130*c* can include a ring electrode 132*c* (FIG. 4) and a transmission member 134*c* (FIG. 5). The ring electrode 132*c* can be adjacent to the anatomical structure, such as the heart 42, to receive electrical signals indicative of the electrical activity of the heart 42. These electrical signals can be transmitted to the ICD 120 via the inner conductor 136*c* of the transmission member 134*c*. The transmission member 134*c* can be disposed in one of the channels 148 of the multilumen member 146.

With reference to FIGS. 3-5, the tip electrode assembly 130*d* can extend beyond the multilumen member 146, and can contact the anatomical structure at a distalmost part, such as the right ventricular apex A of the heart 42. As the tip electrode assembly 130*d* can be generally known in the art, and can be similar to the tip electrode of the SPRINT QUATTRO SECURE™ cardiac lead commercially available from Medtronic, Inc. of Minneapolis, Minn., the tip electrode assembly 130*d* will not be discussed in great detail herein. Briefly, however, the tip electrode assembly 130*d* can include a tip electrode 130*d* and the transmission member 134*d*. The inner conductor 136*d* can electrically couple the tip electrode 132*d* to the ICD 120 so that the tip electrode 132*d* can to receive electrical signals and deliver a therapy, such as a pacing therapy, to the distalmost part of the anatomical structure. As illustrated in FIG. 3, the surface area SA of the tip electrode 132*d* can be smaller than the first surface area A1 of the first defibrillator electrode 132*a* and the second surface area A2 of the second defibrillator electrode 132*b*, and can range from about 1 square millimeter ($mm^2$) to about 8 square millimeters ($mm^2$).

With reference to FIGS. 3-6, in order to assemble the lead 122, in an exemplary process, the transmission members 134 can be inserted into the multilumen member 146. Then, the connection 150 can be coupled to the respective inner conductors 136 to couple the inner conductors 136 to the respective electrodes 132 (FIG. 6). The first conductive braid 144*a* and the second conductive braid 144*b* can then be positioned over the multilumen member 146. Next, the overlay 142 can be formed on, applied or extruded onto the first conductive braid 144a and second conductive braid 144b. The first conductive braid 144a and second conductive braid 144b can then be coupled to the first defibrillator electrode 132a such that the first conductive braid 144a and second conductive braid 144b are in communication with the first defibrillator electrode 132a. In one embodiment, the outer conductive member 144 can be combined with the overlay 142 in a separate operation, such as a continuous extrusion process or a discrete assembly arid heating reflow operation.

With the lead 122 assembled, the lead 122 can be coupled to the ICD 120, and the lead 122 and ICD 120 can be implanted into the anatomical structure. Generally, the lead 122 can be implanted such that the first defibrillator electrode 132a is adjacent to the superior vena cava 44, the second defibrillator electrode 132b is within the right ventricle 42a, and the tip electrode 132d is adjacent to the right ventricular apex A of the heart 42 (FIG. 3). If the anatomical structure encounters an external field, such as that generated by an MRI, a current may be induced in the at least one outer conductive member 144, which can serve to protect or shield the inner conductors 136 from the induced current, and thereby prevent the transmission of the induced current to an electrode assembly with a small surface area, such as the tip electrode 132d.

In this regard, as the at least one outer conductive member 144 covers, surrounds or shields the inner conductors 136 of the electrode assemblies 130, the external field generated by the MRI can induce a current in the at least one outer conductive member 144, thereby protecting or shielding the inner conductors 136 from the effects of the external field. Further, as the at least one outer conductive member 144 is in communication with the first defibrillator electrode 132a, the current and heat induced in the at least one outer conductive member 144 can be dissipated by the first defibrillator electrode 132a into the anatomical structure, which can serve to as a ground for the at least one outer conductive member 144.

While specific examples have been described in the specification and illustrated in the drawings, it will be understood by those of ordinary skill in the art that various changes may be made and equivalents may be substituted for elements thereof without departing from the scope of the present disclosure as defined in the claims. Furthermore, the mixing and matching of features, elements and/or functions between various examples is expressly contemplated herein so that one of ordinary skill in the art would appreciate from this disclosure that features, elements and/or functions of one example may be incorporated into another example as appropriate, unless described otherwise, above. Moreover, many modifications may be made to adapt a particular situation or material to the teachings of the present disclosure without departing from the essential scope thereof. Therefore, it is intended that the present disclosure not be limited to the particular examples illustrated by the drawings and described in the specification as the best mode presently contemplated for carrying out this disclosure, but that the scope of the present disclosure will include any embodiments falling within the foregoing description and the appended claims.

What is claimed is:

1. A method of forming a medical lead system for implantation into an anatomical structure comprising:
providing a lead having a multilumen member passing through the lead, a first electrode in electrical communication with a first inner conductor and fixedly coupled to the multilumen member in a fixed intermediate position between a proximal end and a distal end of the lead, the first inner conductor passing through a portion of the multilumen member, and a second electrode in electrical communication with a second inner conductor and extending beyond an end of the multilumen member in a distal position on the lead, the second inner conductor passing through a portion of the multilumen member, the fixed intermediate position of the first electrode being closer to a longitudinal midpoint of the lead than to the second electrode;
providing the first electrode with a first surface area and the second electrode with a second surface area, with the first surface area being larger than the second surface area;
covering a substantial portion of the lead with a shield; and
electrically coupling the shield to the first electrode.

2. The method of claim 1, further comprising:
providing the lead with a third electrode in electrical communication with a third inner conductor and fixedly coupled to the multilumen member, the third inner conductor passing through a portion of the multilumen member; and
providing the lead with a sensing electrode in electrical communication with a fourth inner conductor and fixedly coupled to the multilumen member, the fourth inner conductor passing through a portion of the multilumen member.

3. The method of claim 2, wherein covering a substantial portion of the lead with a shield further comprises:
covering the lead from a proximal end of the lead to the first electrode with a first conductive member that being in electrical communication with the first electrode; and
covering the lead from the first electrode to the third electrode with a second conductive member that being in electrical communication with the first electrode.

4. The method of claim 2, further comprising:
providing an implantable therapy device;
implanting the therapy device into the anatomical structure; and
coupling the therapy device to the medical lead system such that the therapy device being in electrical communication with the first inner conductor, second inner conductor, third inner conductor and fourth inner conductor.

5. The method of claim 4, further comprising:
providing a programmer operable to be in communication with the implantable therapy device; and
programming the implantable therapy device to deliver a therapy through the medical lead system with the programmer.

6. A method of forming a medical lead system for implantation into an anatomical structure comprising:
providing a lead having a multilumen member passing through the lead, a first electrode in electrical communication with a first inner conductor and fixedly coupled to the multilumen member in a fixed intermediate position between a proximal end and a distal end of the lead, the first inner conductor passing through a portion of the multilumen member, and a second electrode in electrical communication with a second inner conductor and extending beyond an end of the multilumen member in a distal position on the lead, the second inner conductor passing through a portion of the multilumen member, the fixed intermediate position of the first electrode being closer to a longitudinal midpoint of the lead than to the second electrode;
providing the first electrode with a first surface area and the second electrode with a second surface area, with the first surface area being larger than the second surface area;
covering a substantial portion of the lead with a shield; and
electrically coupling the shield to the first electrode by the shield directly abutting the first electrode.

* * * * *